(12) United States Patent
Yu

(10) Patent No.: US 6,200,255 B1
(45) Date of Patent: Mar. 13, 2001

(54) PROSTATE IMPLANT PLANNING ENGINE FOR RADIOTHERAPY

(75) Inventor: Yan Yu, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/182,228

(22) Filed: Oct. 30, 1998

(51) Int. Cl.[7] ........................................ A61N 5/00
(52) U.S. Cl. .................................... 600/1; 600/3
(58) Field of Search .......................... 600/1–8, 427, 600/439; 434/262–275; 378/65

(56) References Cited

U.S. PATENT DOCUMENTS

| | | |
|---|---|---|
| 4,005,699 | 2/1977 | Bucalo . |
| 4,702,228 * | 10/1987 | Russell, Jr. et al. ............... 600/8 |
| 5,373,844 * | 12/1994 | Smith et al. .................... 600/427 |
| 5,391,139 * | 2/1995 | Edmundson ..................... 600/7 |
| 5,740,802 * | 4/1998 | Nafis et al. ..................... 434/267 |
| 5,748,767 | 5/1998 | Raab . |
| 5,752,962 | 5/1998 | D'Urso . |
| 5,797,849 * | 8/1998 | Vesely et al. ................... 600/461 |
| 5,810,007 * | 9/1998 | Holupka et al. ................. 600/439 |
| 5,823,993 | 10/1998 | Lemelson . |
| 5,843,016 | 12/1998 | Lugnani et al. . |
| 5,868,757 | 2/1999 | Koutrouvelis . |
| 5,938,583 * | 8/1999 | Grimm ........................ 600/7 |

OTHER PUBLICATIONS

Yan Yu, "Multiobjective decision theory for computational optimization in radiation therapy" Medical Physics, vol. 24, No. 9, Sep. 1997, pp. 1445–1454.

Yan Yu and M.C. Schell, "A genetic algorithm for the optimization of prostate implants" Medical Physics, vol. 23, No. 12, Dec. 1996, pp. 2085–2091.

* cited by examiner

Primary Examiner—Samuel G. Gilbert
Assistant Examiner—Joseph A. Cadugan
(74) Attorney, Agent, or Firm—Blank Rome Comisky & McCauley LLP

(57) ABSTRACT

An implant planning engine plans implants for radiotherapy, e.g., prostrate brachytherapy. The system optimizes intraoperative treatment planning on a real-time basis using a synergistic formulation of a genetic algorithm, multi-objective decision theory and a statistical sensitive analysis. A total solution for prostate seed implant brachytherapy is achieved.

9 Claims, 12 Drawing Sheets

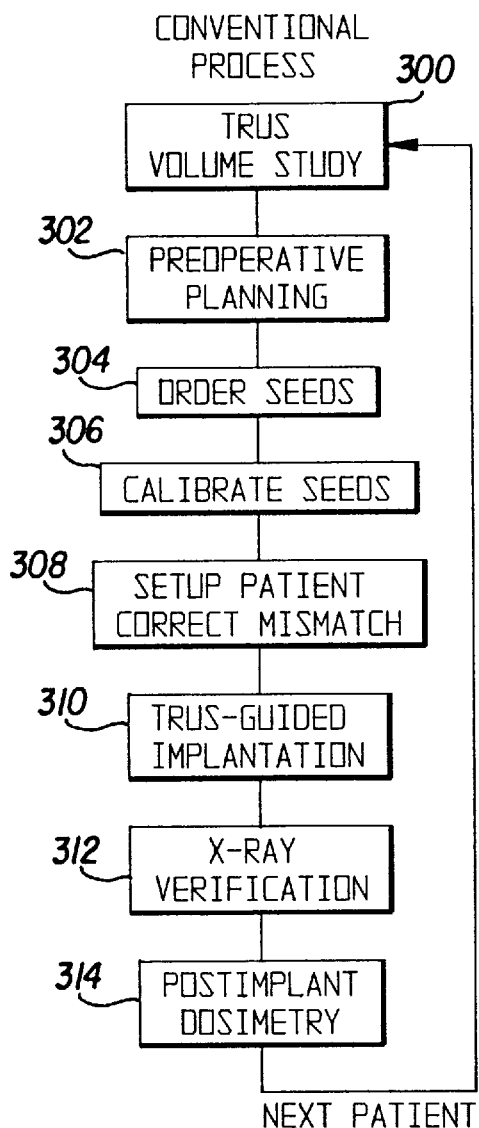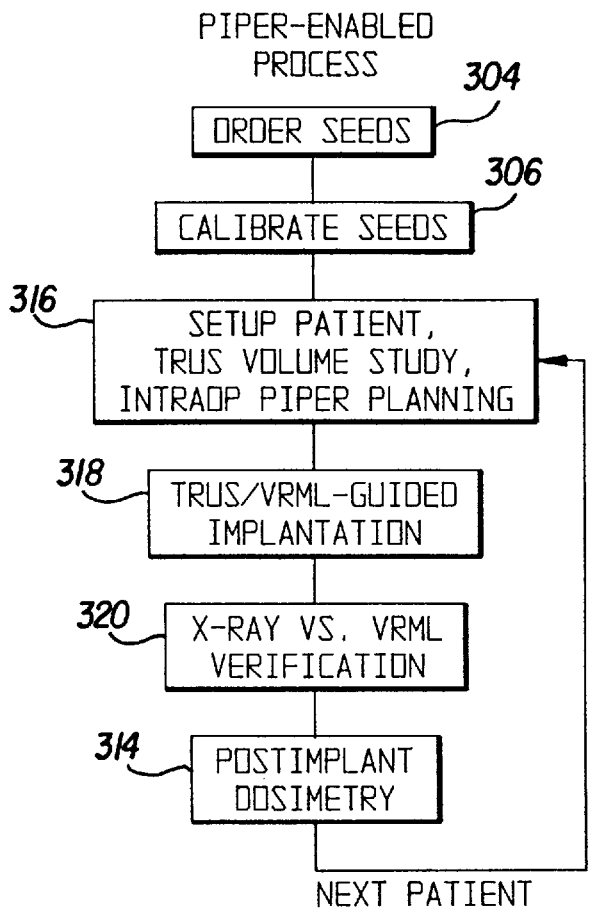
FIG. 3A
FIG. 3B

PROSTATE IMPLANT PLANNING ENGINE FOR RADIOTHERAPY

This invention was made with government support through Grant 1 R43 CA 78115-01 awarded by the National Cancer Institute of the National Institute of Health. The government has certain rights in the invention.

BACKGROUND OF THE INVENTION

The present invention relates generally to the use of a computerized dosimetry system for planning the spatial configuration of radioactive seeds and the associated dose intensity distribution inside and surrounding a planning target volume in the irradiation of cancerous tissue.

More particularly, the present invention relates to a method of and a system for using artificial intelligence to determine the most appropriate seed configuration for a given prostate shape and size, with minimal human intervention.

In the treatment of prostate cancer, a method is often employed to implant numerous radioactive seeds in a carefully preplanned pattern in three dimensions within the prostate. That procedure serves to deliver a known amount of radiation dosage concentrated around the prostate, while at the same time sparing radiation-sensitive tissues, such as the urethra, the bladder and the rectum. Customarily, 60 to 120 seeds are placed through 15 to 30 needles in the inferior (feet) to superior (head) direction (see FIG. 1). These needle positions are selected from a 13×13 grid of 0.5 cm evenly spaced template holes, which are used to achieve precise needle insertion. The number of these holes that intersect with the prostate cross section, and therefore are potentially usable, is typically about 60 (see FIG. 2). The number of mathematical combinations is therefore greatly in excess of $10^{16}$, each of which is a potential treatment plan but is associated with different degrees of cancer control and the likelihood of treatment complications.

In current clinical practice, the design of a suitable seed configuration which is customized to the anatomy of a patient is achieved by a highly trained medical physicist or dosimetrist only by using trial-and-error manual iterations. The practitioner usually starts with an initial needle configuration based on experience or rules of thumb, and then adjusts the radioactive strength per seed or the locations of certain needles or both, until the calculated dose intensity distribution satisfies a set of clinical considerations. That process requires between 15 minutes and 2 hours, depending on the experience of the treatment planner and the geometric complexity of the relationship between the prostate and the surrounding anatomic structures.

These known treatment planning processes are typically aided by one of several available commercial computerized treatment planning systems. Such treatment planning systems enable the user to outline the prostate in relation to a template grid, to turn on or off any available needle positions and seed positions within each needle, and to examine the resultant dose distribution in two or three dimensions. Examples of such planning systems include those offered by Multimedia Medical Systems (MMS) of Charlottesville, Va., SSGI Prowess, of Chico, Calif., Nucletron Plato, from Columbia, Md., Computerized Medical Systems (CMS) Focus, of St Louis, Mo., Radiation Oncology Computer Systems (ROCS), of Carlsbad, Calif., ADAC Laboratory's Pinnacle, of Milpitas, Calif. and Theraplan, available from Theratronics International Ltd. of Kanata, Ontario, Canada.

In a number of such known commercial treatment planning systems, for example, those available from MMS and SSGI, the initial needle configuration that otherwise would have to be turned on by the human treatment planner is automatically set up by the computer system. That initial setup is based on simple rules of thumb, such as uniform loading, peripheral loading or modified peripheral loading. In a number of instances, the manufacturer claims that its planning system offers "automatic planning", "geometric optimization", or "real-time dosimetry". However, none of these commercial planning systems offer true optimization in that the automatically loaded seeds are not designed based on customized dosimetric calculations. Rather, they are designed to fill the space of the prostate in some predetermined manner. Therefore, such known automatic seed loading techniques are designed to save between 15 to 30 mouse clicks by the operator (or about 1 minute of operation). However, the user is still required to apply his or her expert knowledge to iteratively improve upon this initial design in order to achieve customized planning for any individual patient. Thus, there are two significant drawbacks of the above-mentioned current techniques: First, the complete treatment planning process is under the manual guidance of a radiation planning expert using trial and error techniques; and second, the adjustment of the delivered dose is achieved by varying the radioactive strength per seed until an isodose surface with the desired shape and size is scaled up or down to the prescription dose, i.e., these techniques will suffer when the activity per seed is fixed, as at the time of surgical implantation in the operating suite.

Because of these two severe drawbacks, the currently available commercial treatment planning systems are not suitable for intraoperative treatment planning in the surgical suite, where the patient is placed under anesthesia in volatile conditions and where the cost per minute is very high. The variability of human performance, experience and stress, and the general inability of humans to manage large amounts of numerical data in 1 to 2 minutes are also factors that deter current practitioners from performing intraoperative treatment planning.

Although not designed for the express purpose of intraoperative optimized treatment planning, four previously published articles have described methods to automate the dosimetric planning (rather than simple geometric planning) for prostate seed implant brachytherapy. The references, features and deficiencies of these methods are as follows:

1. Roy J N; Wallner K E; Chiu-Tsao S T; Anderson L L; Ling C C. ["CT-based optimized planning for transperineal prostate implant with customized template." *International Journal of Radiation Oncology Biology and Physics*, 21:483–9 1991] This is an early attempt at computerized optimization and automation of dosimetric planning. The authors start from a manual design of the needle configuration, and use a least square computer algorithm to find the best seed loading pattern within the needles. The major limitation of this approach is that once the needle pattern is fixed by the human planner, only superficial degrees of freedom exist for the computer algorithm to optimize the dosimetry. For example, only the seed spacing within each needle can be varied, which is inconsistent with the standard technique of 1 cm uniform spacing. In addition, the least square optimization method is known to be unable to search widely for the best overall treatment plan in this multi-modal problem; it tends to settle for the nearest local optimal solution because there is no mechanism to test other design patterns which initially may be suboptimal. In general, any optimization method that presumes an existing fixed needle configuration (either designed manually by the dosimetric planner or automatically loaded based on geometric rules) does not allow sufficient variation in the possibilities of dose distribution to produce the optimal treatment plan.

2. Yu Y; Schell M C. ["A genetic algorithm for the optimization of prostate implants." *Medical Physics*, 23:2085–91 1996] This is the first attempt in using an "intelligent" computer algorithm, viz., the genetic algorithm, to explore the world of dosimetric possibilities for prostate brachytherapy planning. It is a theoretical work, not directly applicable to real-life prostate shapes and sizes. In fact, the prostate is schematically represented by ellipsoids of various sizes and elongations. The genetic algorithm is of an off-the-shelf generic kind, where the template is linearized into a string of bits, and not encoded by two dimensional genetic templates such as in the present invention. The article describes the use of a utility function for dosimetric comparison of competing treatment plans, which later turns out to be applicable only to one type of isotope and only to the prostate. In contrast, the present invention uses a multi-objective decision process to compare treatment plans in different aspects, such as dose to the prostate, urethra, rectum, and the sensitivity of the dose to surgical seed placement uncertainties. For these reasons, the method described in this article cannot be used under real-life clinical conditions.

3. Pouliot J; Tremblay D; Roy J; Filice S. ["Optimization of permanent $^{125}$I prostate implants using fast simulated annealing." *International Journal of Radiation Oncology Biology and Physics*, 36:711–20 1996] These authors apply simulated annealing, an optimization method commonly said to be inferior to genetic algorithms, to optimize prostate seed implant treatment plans. Their method is slow, requiring 15 minutes of run time on a workstation and tens of thousands of iterations to converge. In its scheme for comparing different treatment plans for quality, they assign a simple weighting factor to each of the terms in a cost function to represent its relative importance. In contrast, the present invention employs multi-objective optimization incorporating goals and satisfying constraints to produce the optimal plan in 1 to 2 minutes.

4. Chen Y, Stanton R E, Holst R J, Koprowski C D, Krisch E B. ["Treatment planning for prostate implant with loose seeds," *Medical Physics* 24:1141–1145 1997.] These authors use an ad hoc method to add one seed at a time into a prostate implant plan, until a single parameter that measures an aspect of the dosimetric quality approaches a broad minimum, signifying convergence. The method achieves automation by successively putting seeds into the location of the lowest dose inside the prostate. While this ad hoc method appears rational, it in no way performs optimization because the point of lowest dose at any instance during the progression of planning is not necessarily the final region of low dose, by virtue of the summation of doses from 60 to 120 other seeds.

In the broad area of genetic algorithms and optimization methodology, there have been a large number of articles which have described general and/or specific problems and solutions either in abstract or in concrete examples. Some of the well-known writings include those by Holland [Holland J H, Genetic algorithms, *Scientific American* 267:66–72, 1992] and by Goldberg [Goldberg D E, *Genetic Algorithms in Search, Optimization and Machine Learning* (Addison-Wesley, Reading, Ma., 1989)]. Even multi-objective optimization in the context of genetic algorithms have been described. Among these is an article written by the present inventor [Yu Y, "Multiobjective decision theory for computational optimization in radiation therapy," *Medical Physics* 24:1445–1454, 1997], using idealized prostate seed implants and idealized stereotactic radiosurgery as test cases. However, none of these prior methods address the unique two-dimensional nature of the template and the three-dimensional nature of the seed distribution, which bear important consequences to the optimization speed for prostate brachytherapy planning and thus its usability in the surgical suite. In addition, none of these prior methods use the accelerated n-tournament selection as described in the present invention, which also contributes to the speed of the present optimization system.

It is also important to have the capability of navigating the implantation scene on a three-dimensional basis. To that end, the prior art systems described above, such as that available from MMS and indeed all other commercial systems, use common 3D computer graphics for visualizing the prostate and the seed trains, as well as for inspecting the isodose surface. On the other hand, the present invention makes use of the Virtual Reality Modeling Language (VRML) to build an interactive navigational scene of surgery whose function is to guide needle insertions in real-time, to interrogate the anatomy of the patient, to alter the display state of the needles from unimplanted (emissive in color), to being implanted (pulsating colors), to implanted (dull color), and to serve as a verification tool at postoperative fluoroscopic imaging of the implant.

The standard procedure of a prostate seed implant before the advent of the instant Prostate Implant Planning Engine for Radiotherapy (PIPER) system of the present invention will now be described with reference to FIG. 3A. Having chosen a prostate implant as the treatment option of choice, the patient is subjected to a transrectal ultrasound (TRUS) volume study. That enables the treatment planning team (1) to determine the cross-sectional shape of the prostate on consecutive slices at 5 mm intervals from cranial (head) to caudal (feet) directions; (2) to overlay those prostate contours onto a template pattern that mimics the transperineal template used to guide the implantation; and (3) to get a measure of the total volume of the prostate. Often, the patient also undergoes a CT examination to make sure that the pubic bones do not interfere with the paths of the needle positions that must be chosen in the treatment plan.

The medical physics staff then takes the TRUS volume study information, inputs it into the treatment planning computer, and develops an acceptable treatment plan through a trial-and-error process that improves upon a set of treatment objectives. This treatment planning step allows the number of seeds and the radioactivity strength per seed to be determined, at which time the seeds can be ordered for this patient. A typical plan calls for 60–120 seeds. When the seeds arrive, which currently takes about 3 months, the medical physics staff performs a calibration check on the seed batch.

On the day of implantation, the patient is anesthetized and positioned on the operating table in a position which as closely as possible matches the position of the prior TRUS volume study. That position is verified under TRUS by viewing the same cross-sectional images of the prostate as in the volume study, in relation to the actual implantation template. The common difficulties with that approach are (1) the prostate often has changed size and/or shape; and (2) the prostate cannot be put in the same position with respect to the template as in the treatment plan. Those problems are now widely recognized by brachytherapy practitioners. It is generally acknowledged (for example, by the American Association of Physicists in Medicine Task Group No. 64 on Prostate Seed Implant Brachytherapy) that intraoperative computerized treatment planning is the only solution that overcomes these problems.

Ideally, when the prostate position on the template matches that of the preoperative plan, the implant proceeds exactly as prescribed by the plan. When all the seeds are placed, an x-ray image is taken in the operating room to confirm that the seed pattern is in reasonable agreement with expectations. Approximately 1 month thereafter, the patient returns for a CT examination of the implant. The CT information is transferred to the treatment planning system for postimplant dosimetry.

While the human treatment planning described above typically takes 2 hours per patient, the PIPER system of the present invention automatically generates optimized treatment plans customized to the patient in 2 minutes or less (based on 333 MHZ Pentium II PC speed). In addition to achieving improvements in the treatment plan quality as well as savings in human effort, the speed of the PIPER system of the present invention allows multiple patient management steps to be consolidated (see FIG. 3B). Thus, a batch of seeds can be periodically ordered for a stream of patients; eligible patients can be scheduled for implantation without delays due to preoperative planning and seed ordering; patient setup, TRUS volume study and treatment planning are combined to a single step, referred to as intraoperative planning, all performed in the operating room minutes before seed placement; matching of prostate position is no longer needed; and changes in prostate size and shape between planning and implantation are avoided.

In effect, the PIPER system of the present invention achieves a what-you-see-is-what-you-get (WYSIWYG) environment in the operating room. Still another added benefit is that since seeds are ordered in a batch for many patients, the safety margin (around 10–15%) of extra seeds previously ordered for each patient can now be shared, leading to a reduction in the number of wasted seeds (at $30–40 per seed), and thus a reduced cost.

After conducting a clinical study on ten consecutive implant patients on intraoperative optimized planning using the PIPER system of the present invention, the inventor has reached the following conclusions regarding the advantages of the present invention:

Intraoperative planning using the PIPER system of the present invention produces treatment plans of comparable quality to those from preoperative planning using the PIPER system of the present invention (which was shown in two previous studies to be superior to other planning techniques);

Intraoperative planning is logistically feasible;

Intraoperative planning significantly reduces ad hoc changes necessitated by prostate volume change. Using the known conventional technique, an average of 68% of the planned seed positions had to be modified. Under intraoperative planning with the PIPER system of the present invention, only 7% of the planned seed positions received minor modifications.

Because of less changes, the overall time in the operating room as recorded by the anesthesiologist was shorter by 11% using the PIPER system of the present invention. That is a significant cost saving since the OR time is usually charged by the minute.

Most of the participating clinicians scored their experience using the PIPER system of the present invention as better than their experience with the conventional preoperative experience.

The technology of the PIPER system of the present invention is built upon a synergistic formulation of a genetic algorithm, multi-objective decision theory and a statistical sensitive analysis.

The genetic algorithm is a method of intelligent computation, which has been applied in areas of artificial intelligence, engineering, defense, business and finance. The implementation of the genetic algorithm for brachytherapy is a unique aspect of the system of the present invention. It is the only optimization methodology presently known to have a demonstrated effectiveness for prostate seed implants. It uses a cooperative-competitive environment (coopetition) for potentially desirable treatment plans to most efficiently evolve to a single dominant pattern. Among the evolution processes implemented by the system of the present invention are sexual reproduction from parent patterns, mutation of the offspring, and competitive repopulation.

The multi-objective decision theory and sensitivity analysis used by the system of the present invention were formulated based on simulated annealing and stochastic computation. When coupled to the genetic algorithm, the multi-objective decision module ensures that the computer system's candidates for the optimal treatment plan are consistent with the clinicians' preferences and judgment. The sensitivity analysis module of the system of the present invention ensures that the chosen treatment plan is optimal, not only in the ideal configuration, but also after surgical uncertainties occur. The interplay of these three components of the PIPER system of the present invention provides a total solution for real-time intraoperative planning, where traditional manual planning under severe time-constraints and human pressure is simply not feasible.

SUMMARY AND OBJECTS OF THE INVENTION

In view of the foregoing, it should be apparent that there still exists a need in the art for a method of and a system for accurately and efficiently determining the most appropriate seed and needle configuration for use in treating a cancerous prostate. It is, therefore, a primary object of this invention to provide a method of and apparatus for performing intraoperative treatment planning in real-time in a surgical suite and which provides optimized treatment planning for prostate seed implant brachytherapy.

More particularly, it is an object of this invention to provide a method of and system for providing optimized intraoperative treatment planning on a real-time basis in a surgical suite for radiation treatment of the prostate in which a customized patient treatment plan is generated in a much shorter time than with known prior art methods.

Still more particularly, it is an object of this invention to provide an optimized real time intraoperative prostate implant planning system in which any systemic errors between the planned seed positions and the actual seed placement locations are eliminated, based on the actual observation of needle locations using real-time ultrasound images.

A further object of the present invention is to provide a prostate implant planning engine for radiotherapy in which, on an intraoperative planning basis, the degree of pubic arch interference is determined and is utilized to ensure that proper placement of the seeds and needle implants is attained.

Briefly described, these and other objects of the invention are accomplished using a synergistic formulation of a genetic algorithm, multi-objective decision theory and a statistical sensitive analysis. The interplay of those three components of the prostate implant planning engine for radiotherapy system of the present invention provides a total solution for real-time intraoperative planning. Using the PIPER system of the present invention, a batch of seeds is periodically ordered for a stream of patients and eligible patients are then scheduled for implantation without any delays due to preoperative planning and seed ordering. Each patient is then set up, and the TRUS volume study and treatment planning are combined into a single intraoperative planning step, intraoperative planning is performed in real-time in the operating room minutes before seed placement. Since the system of the present invention is conducted in real-time, a WYSIWYG environment is achieved in the operating room which eliminates the matching of prostate position and changes in prostate size and shape problems inherent in prior methods which required separate planning and implantation steps, sometimes months apart.

In its planning aspects, the PIPER system of the present invention reads the anatomy data previously generated and determines the maximum extent of the prostate size, as well as the degree of pubic arch interference. The preference profile of the clinician-users is then read from a profile file and such data is used to influence the baseline priorities of optimizing different objectives, such as the dosing of the prostate, keeping the number of needles to a minimum, etc. The dosimetry values are then looked up for each chosen seed. Then, the two-dimensional genetic algorithm for the prostate is encoded, thus encoding the location of all potential needle placement positions, using a two-dimensional binary pattern. A population pool with a random population is then initiated and the dosimetry for each member of the population is evaluated. Members of the population are then ranked using multi-objective metrics and a dynamic n-tournament analysis is performed on the ranked members. After performing a two-dimensional crossover and a mutation, the optimal solution of needle and seed locations is obtained.

The PIPER system of the present invention also provides various displays which show different navigational angles for surgical navigation, which displays are automatically generated upon completion of the planning engine and the generation of the optimal solution for the location of the seeds and placement of the needles. The virtually reality navigational model allows clinicians to obtain a visual confirmation of needle placement within the prostate as well as allowing a comparison, at the end of the implantation procedure, between the anterior-posterior view of the prostate and images obtained from a mobile overhead x-ray fluoroscopy machine, in order to facilitate the discovery of any regions of under-dosage due to unintentional seed migration. It likewise provides confirmation that the implant has proceeded as planned.

BRIEF DESCRIPTION OF THE DRAWINGS

FIG. 3A is diagram of a flow chart which illustrates a conventional preplanned implantation process;

FIG. 3B is a diagram of a flow chart which illustrates the PIPER-based intraoperatively planned implantation process of the present invention;

DETAILED DESCRIPTION OF THE PREFERRED EMBODIMENT

Figure 1:
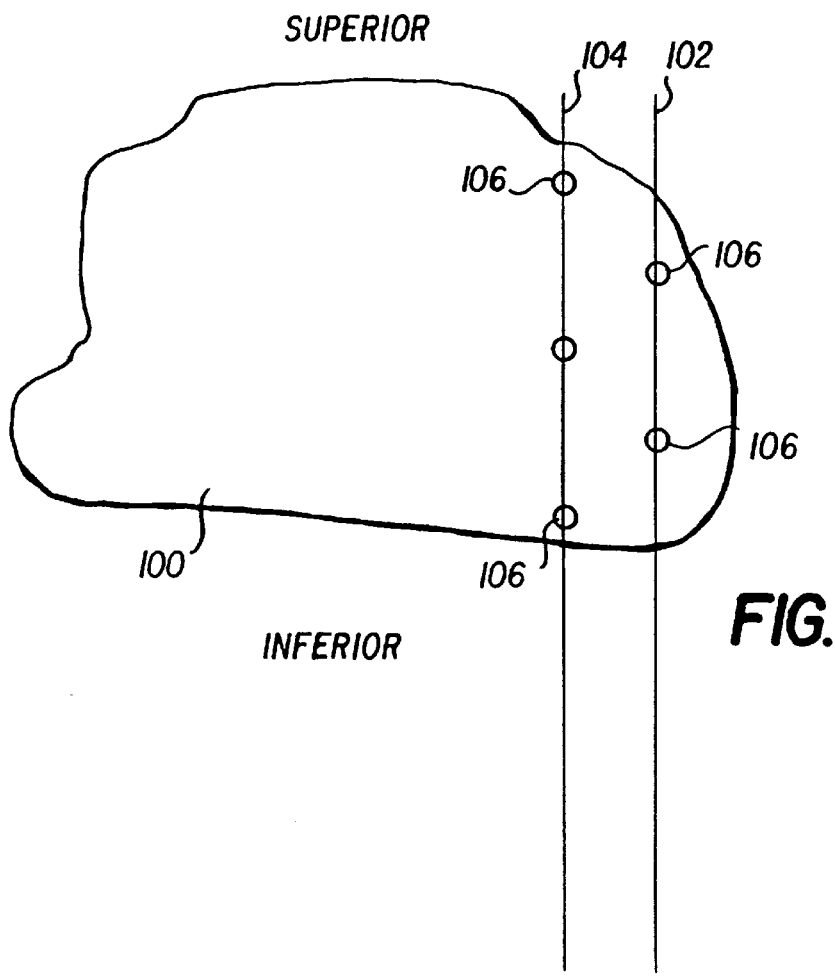
FIG. 1 is a schematic drawing showing two possible ways to load seeds within a needle. Typically, the maximum number of seeds at 1 cm fixed spacing are loaded within each needle, resulting in possibly staggered planes of seeds in the prostate volume.

Referring now in detail to the drawings, in which like elements are indicated by like reference numerals throughout, there is shown in FIG. 1 a drawing of a cross section of a prostate 100 into which two needles 102, 104 are placed. The needles 102, 104 are loaded with seeds 106 which are used to irradiate the prostate tissue 100. Typically, the seeds 106 are spaced at fixed positions 1 cm apart in each of the needles 102, 104. As shown in FIG. 1, the seeds 106 can be loaded within the needles 102, 104 in such a manner that the seeds occupy staggered planes within the prostate volume 100.

Figure 2:
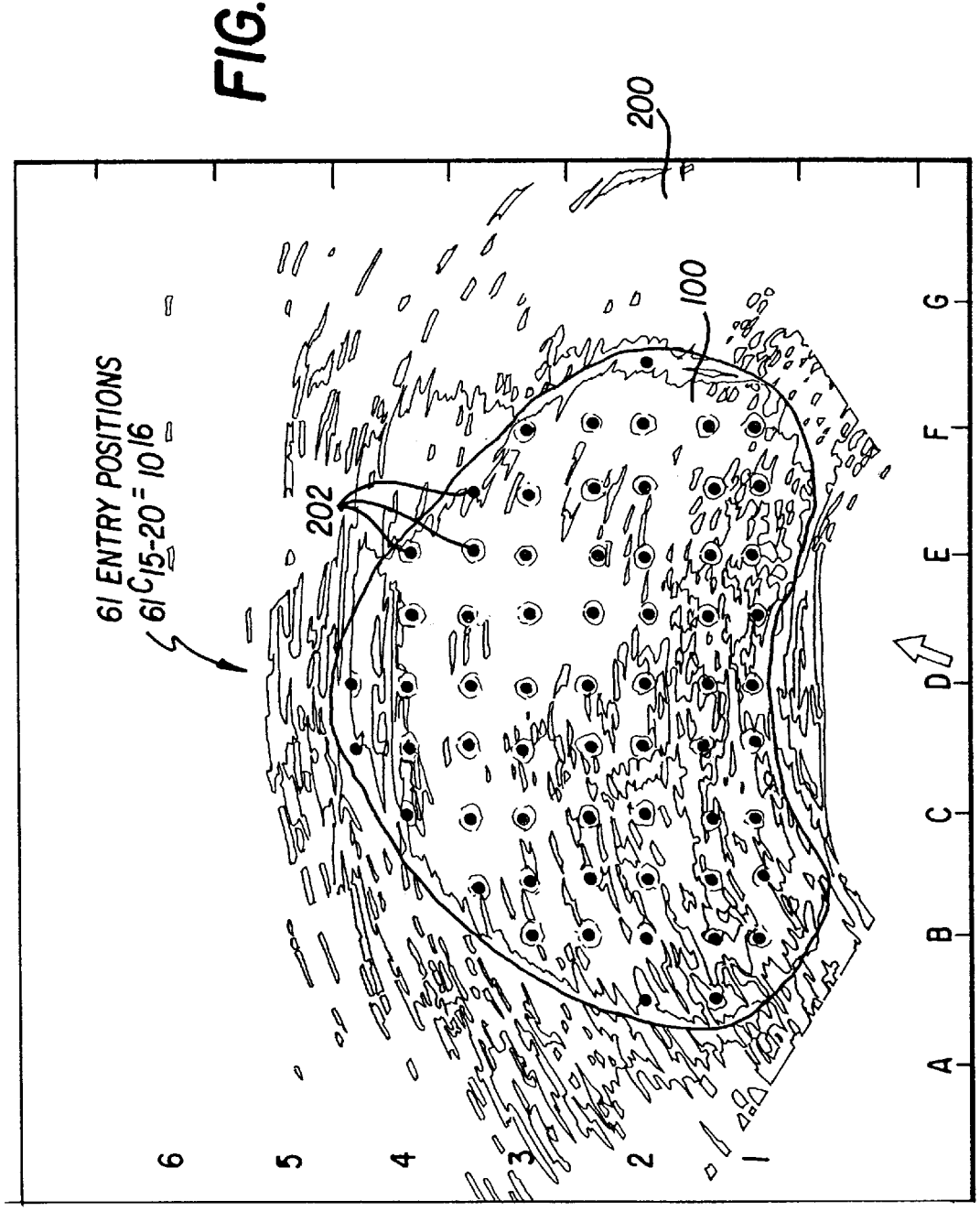
FIG. 2 is a drawing of an ultrasound image of a prostate showing a single cross-sectional view, the template coordinates, outline of the prostate at this position, and those template holes that fall within the maximum projection of the prostate.

FIG. 2 is a drawing of an ultrasound image of a prostate 100 and shows a single cross sectional view. The prostate 100 is shown on a template 200 which contains a number of holes 202 spaced about the template through which the needles 102, 104 shown in FIG. 1 pass. The template 200 is placed over the prostate 100 image so that the maximum number of holes 202 are contained within the outline of the prostate 100. Treatment planning for this clinical case would require $10^{16}$ or more possibilities for seed placement.

FIGS. 3A and 3B are diagrams of two flow charts, one showing a conventional preplanned implantation having steps 300–314 (FIG. 3A) compared to the PIPER system intraoperatively planned process of the present invention having steps 304, 306, 314, 316 and 316–320 (FIG. 3B). As shown for the conventional process in FIG. 3A, the TRUS volume study is first conducted at step 300, followed by the preoperative planning at step 302. Then, the seeds are ordered at step 304 and calibrated at step 306. Next, the patient is setup and any mismatches of the prostate position between the TRUS volume study and the setup are corrected, at step 308. Then, a TRUS-guided implantation of the seeds is conducted at step 310. After x-ray verification of the seeds and needle position at step 312, the postimplant dosimetry proceeds at step 314. The next patient is then treated using the same procedure.

In the PIPER-based intraoperatively planned implantation process shown in FIG. 3B, the seeds are ordered at step 304 and then calibrated at step 306, both in a known manner. Then, the patient is setup, the TRUS volume study is performed and intraoperative planning is performed, all at step 316. Next, implantation of the needles 102, 104 containing the seeds 106 is performed, guided by both the TRUS and VRML techniques, at step 318. After x-ray and VRML verification at step 320, postimplant dosimetry of the prostate 100 occurs at step 314.

Figure 4:
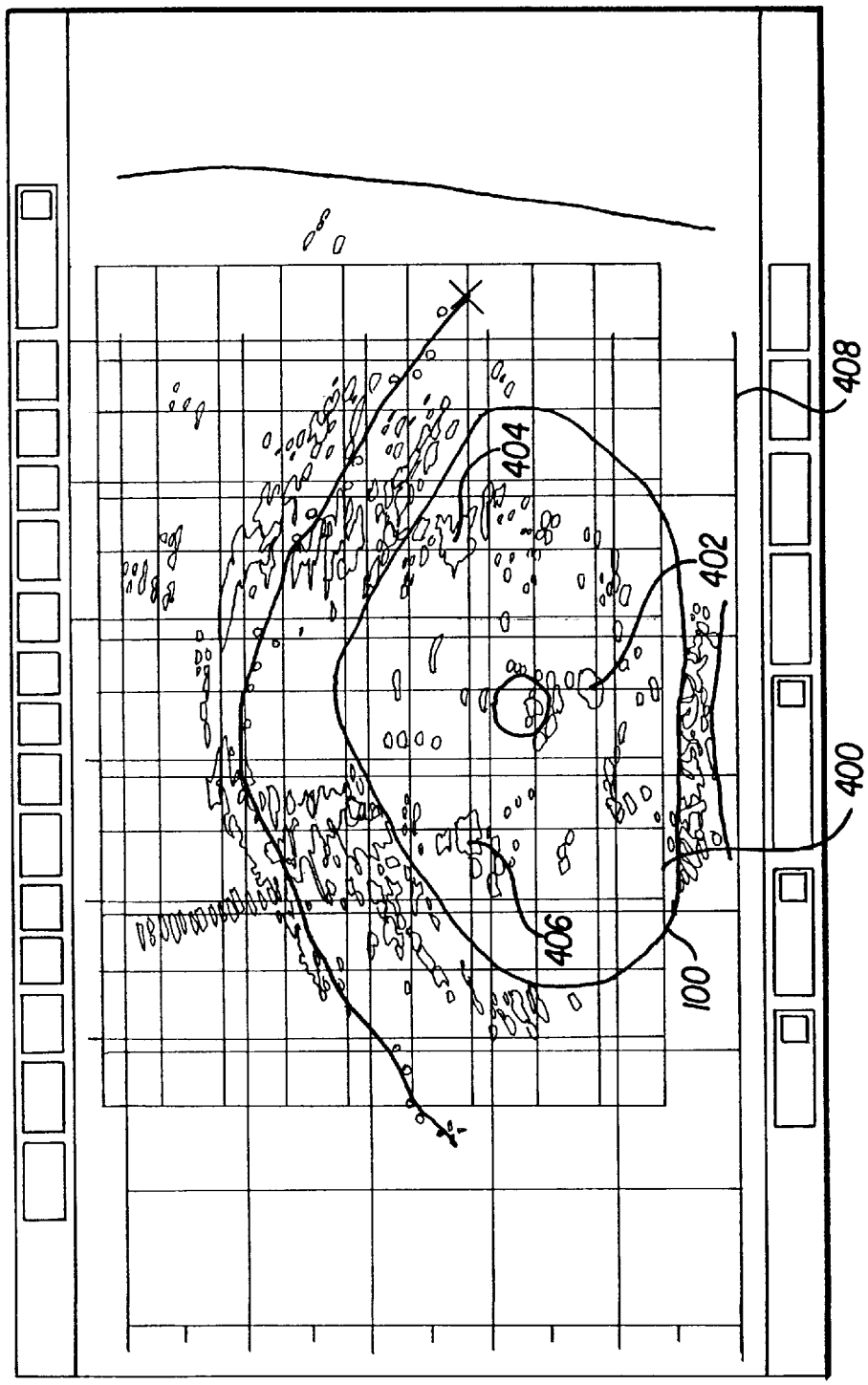
FIG. 4 is a drawing of the unique system of the present invention for registering the template coordinates with the actual locations of the stabilizing needles observed under ultrasound imaging.

FIG. 4 is a drawing of an ultrasound image of the prostate 100 which is visualized with three stabilizing needles 400, 402 and 404 inserted as shown by the hyperechoic locations on the ultrasound image. The colored grid template 406 of the PIPER software is offset from the gray grid ultrasound generic template 408 to account for a small amount of mismatch between the needle tracks and the generic template 408. If left uncorrected, this offset generally leads to systematic errors between the planned seed positions and the actual seed placement locations, resulting in an under-dosage of part of the cancerous prostate. Systematic errors such as these are a common clinical finding. There is no prior art system which is known to provide a solution to this problem based on the actual observation of needle locations on real-time ultrasound images.

The drawing of the prostate and other anatomies can be by discrete points, or by continuous curves. In the latter case, the density of the representative points for each anatomy is automatically down-sampled to avoid over-computation. The digitized anatomy data are saved separately from the grayscale image data, such that the superior-inferior position relationship is preserved between the two.

Figure 5:
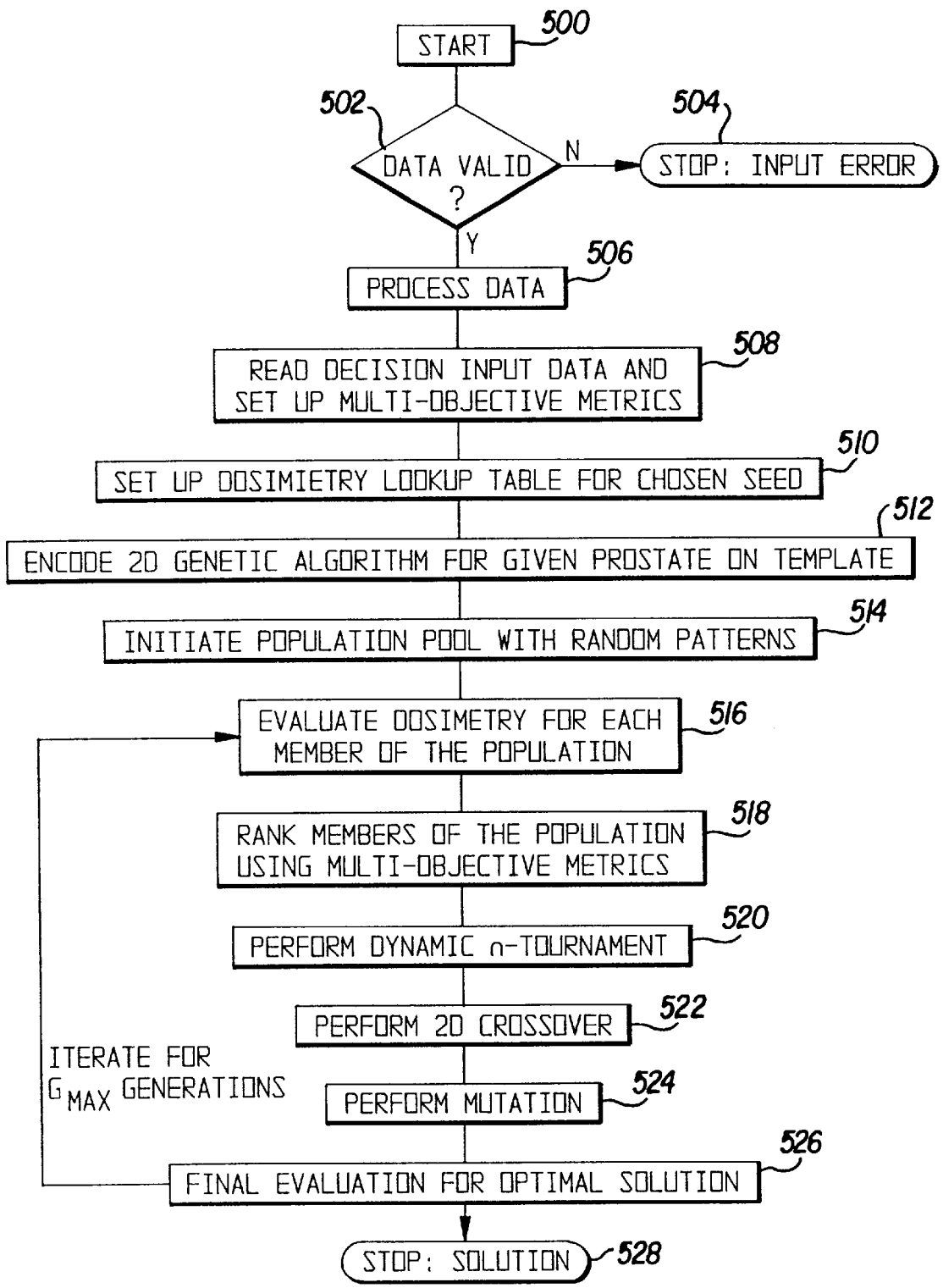
FIG. 5 is a diagram of a flow chart of the genetic algorithm optimization system of the present invention.

Referring now to FIG. 5, there is shown, in flow chart form, a diagram of the planning engine of the present invention that utilizes a two-dimensional genetic algorithm coupled to the multi-objective decision theory, which enables real-time optimized planning for prostate seed implants.

The planning engine starts at step 500, Then, at step 502, the program reads the anatomy data generated as described in connection with FIG. 4, and then determines the integrity and validity of the data. If it is determined at step 502 that the data is not valid, then an error condition is generated at step 504 and the program stops.

At step 506, the anatomy data is down-sampled, so that any two adjacent points on a contour will not be closer than 2 mm. The down-sampled anatomy data is used to determine the maximum extent of the prostate size, which is a major determinant of dosimetry complexity. In addition, the degree of pubic arch interference is also determined at this time. It should be noted that a high degree of pubic arch interference is a clinical contra-indication for implantation. However, no prior art system is known which determinations the percentage of pubic arch interference in real-time.

The decision input data is read at step 508 and the multi-objective metrics are set up. This step involves reading a "preference profile" of the clinician-user(s) from a profile file. Such preferences influence the baseline priorities of optimizing different objectives, such as the dosing of the prostate, sparing the urethra or rectum, keeping the number of needles used to a minimum etc., as well as goals and satisfying values for those objectives. Those preferences are fed as inputs to the multi-objective decision theory such that they reflect the choices of a clinician team. They are not subject to frequent changes.

The dosimetry lookup table is then set up for the chosen seed at step 510. In order to obtain a fast computation, the dose from a single seed of a given type is pre-computed in 0.01 cm increments up to a distance of 41 cm, which is more than half the width of a typical pelvis. The computations are saved to a vector array in computer memory. Subsequent dose summation from multiple seeds at any location is then achieved via vector array lookup indexed by the distance.

At step 512, the two-dimensional genetic algorithm is encoded for a given prostate on the template. Unlike prior genetic algorithms, the PIPER system of the present invention encodes the location of all potential needle placement positions (template holes 202) using a two-dimensional binary pattern, and not a linearized "chromosome" or "gene". This is a significant advancement of the algorithm, which results in an efficient and high quality genetic evolution towards the optimal needle configuration on the given template.

A population pool with a random population is then initiated at step 514. In order to achieve the maximum exploration of all combinations of needle patterns, the genetic algorithm population, which is usually set to the size of 64, is initiated to random patterns, on average turning on every fourth needle position on the 2D template pattern space 200. In instances in which the clinician-users have a strong preference in one of the genetic loading patterns, such as peripheral loading or uniform loading, such pattern is introduced into the initial population pool with greater representation.

As discussed above, the drawing of the prostate and other anatomies can be by discrete points, or one of the generic loading patterns, such as peripheral loading or uniform loading. In any event, the pattern used is introduced into the initial population pool with greater representation. At step 516, the dosimetry for each member of the population is evaluated. Multiple dosimetric parameters are evaluated separately for each of the needle/seed configurations in the population, using the dose lookup vector array and three-dimensional distance computation. Thus, dose D vs. distance r from a single seed is pre-tabulated as a lookup table, with each entry corresponding to 0.01 cm$^2$ in r$^2$. The dose contribution from seed i to point j is then equal to $$D[(x_i-x_j)^2+(y_i-y_j)^2+[(z_i-z_j)^2].$$

Much computation time can be saved by avoiding calculating square roots or calculating dose for each pair of seed and dose point.

Members of the population are then ranked using multi-objective metrics at step 518. In this step, the multiple parameters of dosimetry are combined using the dynamic $L_p$ metric as described in a previous publication [Yu Y, "Multiobjective decision theory for computational optimization in radiation therapy," *Medical Physics* 24:1445–1454, 1997], which is incorporated by reference herein. The purpose of this module is to produce an ordinal ranking of the treatment plans comprising the current population.

Next, a dynamic n-tournament is performed, at step 520. In a regular n-tournament operation, the best of n randomly chosen candidates in the population is allowed to replicate into the next generation. That simple scheme for natural selection based on "fitness" produces slow convergence that is unacceptable to real-time operating room use. The PIPER system of the present invention thus introduces a significant modification to this known scheme, termed "accelerated n-tournament". After every N generations, n is incremented by 1 up to one-fourth the population size. The accelerated n-tournament allows the planning engine to converge in a medium horizon suitable to intraoperative use.

A two dimensional crossover is then performed, at step 522. In prior genetic algorithms, crossover refers to breaking up two linear "chromosomes" at the same location(s) and exchanging the corresponding fragments. The PIPER system introduces the 2D crossover, which is designed to accommodate the 2D encoding scheme of the implantation template 200. It operates as follows. Each row of encoded bits on the enclosed template experiences a separate and independent crossover, thus preserving the two-dimensional nature of the problem and yet effecting an efficient evolutionary mating mechanism.

After a 2D crossover is performed, a mutation is then performed, at step 524. In this step, each bit of the enclosed template pattern is assessed randomly such that there is a predetermined probability $P_M$ that the needle pattern will change from on to off or vice versa. Such random mutation allows the treatment plans consisting of certain needle configurations to change instantaneously, by deleting or adding needles. A mutation which leads to a poorer plan will then have a high likelihood of being eliminated by virtue of the n-tournament, whereas a successful mutation will introduce new patterns into the solution pool. After step 524, an interaction for $G_{max}$ generations is performed. The genetic algorithm subsystem is thus allowed to iterate for $G_{max}$ generations, as prescribed by the user. Early convergence is possible (by setting a program flag) when a predetermined number of generations yield the same best solution. Thus, steps 516 through 524 are performed until the best solution is obtained. The best solution is considered achieved when the same needle configuration is ranked the highest quality among the population in $G_{max}/20$ successive generations, i.e., no additional improvement has been observed in $G_{max}/20$ successive generations.

A final evaluation for the optimal solution is then performed at step 526. As an option, this step may be performed on the best solution in each generation to determine a final optimal solution, using the baseline multi-objective ranking metric and any satisfying conditions imposed by the user. Having thus determined the optimal solution, the program stops at step 528. The optimal solution is then decoded into seed configuration coordinates, needle template coordinates, and the corresponding dosimetric parameters, to be presented to the clinician-user(s).

Figure 6A:
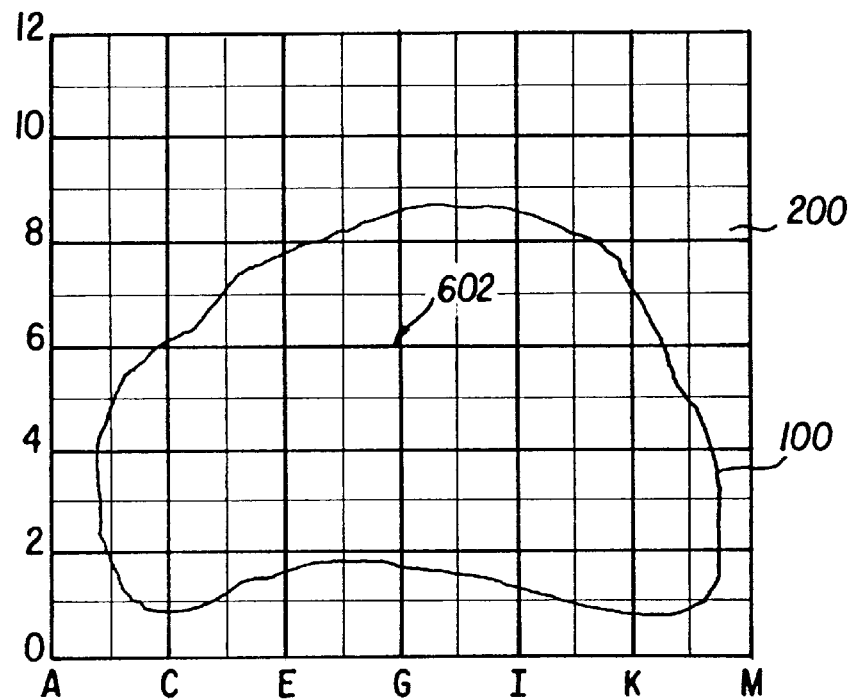
FIG. 6A is a drawing showing a two-dimensional genetic algorithm encoding schematic of a prostate outline on a given template for use with the system of the present invention.
Figure 6B:
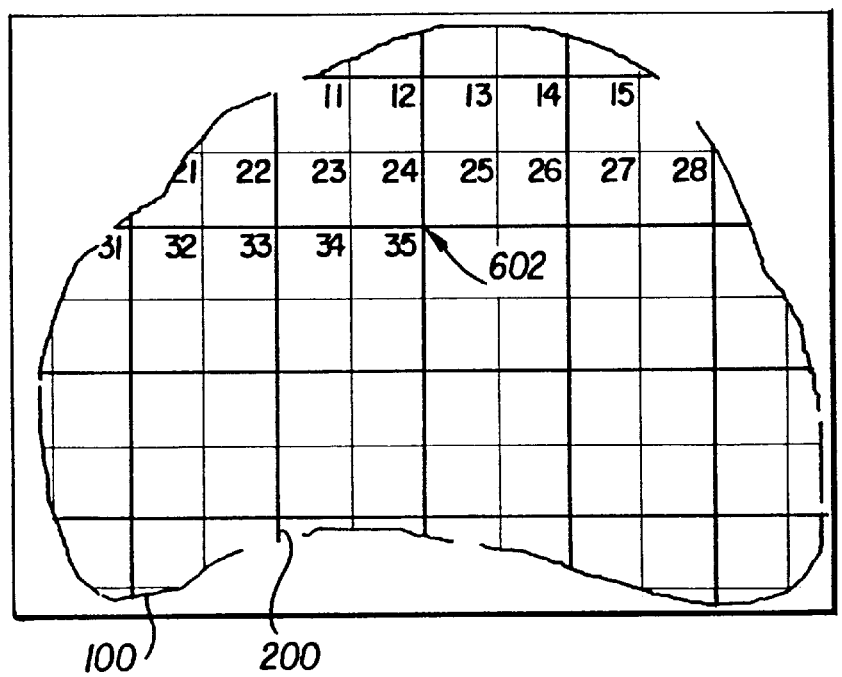
FIG. 6B is a drawing showing a two-dimensional genetic algorithm encoding schematic of a reduced template space for 2D encoding with variable bits per row of template holes for use with the system of the present invention.

Referring now to FIG. 6A, there is shown a drawing of the largest cross-sectional projection of the prostate 100 in the superior-inferior direction overlaid onto the implantation template 200. FIG. 6B shows the template space reduced to those locations that are enclosed by the cross-sectional projection of the prostate 100 of FIG. 6A, which are potentially usable by the clinicians for implantation. The resulting encoding scheme is a variable width 2D matrix array, which replaces the conventional "chromosome" or "gene" representation of a linear string of bits. The matrix is denoted $K_{ij}$. The number of available needle positions on row i is denoted $L_j$. Referring to FIG. 6B for the first row of the template, $L_1=5$, and $K_{1j}$ (j=1 . . . 5) are shown. Similarly, the second row has $L_2=8$, with $K_{2j}$ (j=1 . . . 8), representing the labeled positions. The physical coordinates of each given encoded position, e.g., $K_{ij}$, are stored in a predetermined way of $x_{ij}$ and $y_{ij}$ which are fixed in space. As an example, the position $K_{35}$ has $x_{35}=3$, $y_{35}=3$ (refer to FIG. 6A), with $K_{35}=1$ indicating the template position 602 contains a needle, or $K_{35}=0$ to indicate that the position does not contain a needle.

The genetic algorithm therefore only manipulates the matrix K, with the possible values of 0 and 1.

Figure 7:
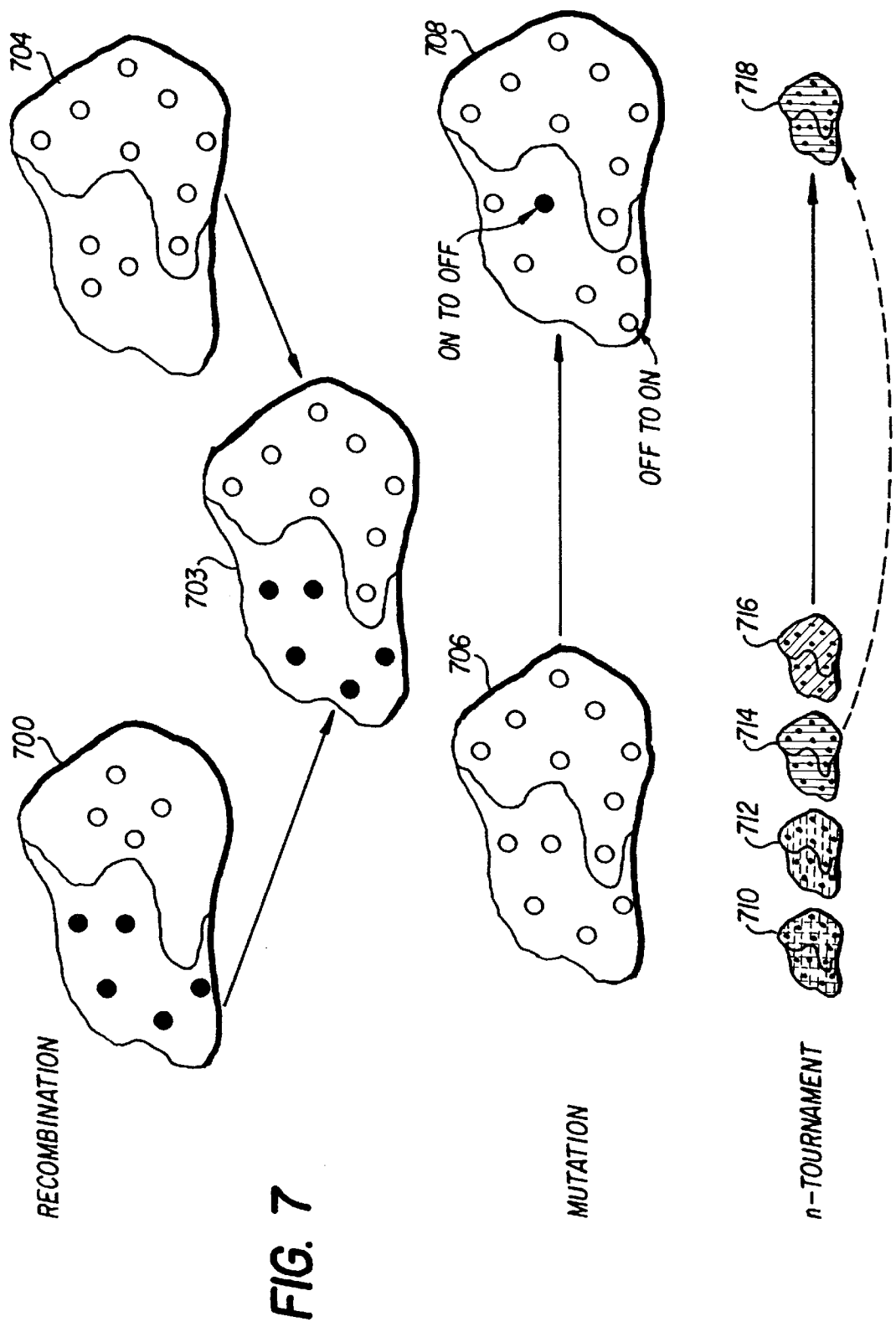
FIG. 7 is a drawing of the genetic algorithm operators used with the system of the present invention: 2D recombination, 2D mutation and accelerated n-tournament.

FIG. 7 is a drawing illustrating the genetic algorithm operators used with the PIPER system of the present invention. In a recombination operation, shown by elements 700–704, a stochastic break line is generated across the anterior (front)-posterior (back) direction, fragmenting each of the two chosen configurations 700 and 704 into two or more sub-solutions 702. In that case, the left side of the configuration 700 on the left is subsequently combined with the right side of the right configuration 704, resulting in a new treatment plan. A recombination operation is also referred to as 2D crossover.

Mathematically, the location of the breakpoint on row i is determined each time by:

$$B_i = nint(q \times (L_i-1))+1,$$

where q is a floating point random number in the range between 0 and 1, and $L_i$ as before is the number of locations in row i. A new random number is generated each time q is used, the value of which depends on the computer system.

After extensive experimentation, it has been found that the parameter combination that guarantees a consistent optimal result is (probability of crossover)$p_c=0.6$, (probability of mutation) $P_M=0.1$, (maximum generation number) $G_{max}=200$, and (population size) P=64.

In a mutation operation, an example of which is shown in the middle of FIG. 7, an original needle location from element 706 that was "on" (insert needle there) undergoes mutation and becomes "off" in element 708; similarly, an original needle location that was "off" (no needle there) in element 706 undergoes mutation and becomes "on" in element 708. These apparently minor changes lead to drastic differences in the resulting dosimetry of the mutated treatment plan, and are responsible for introducing new genetic patterns into the evolving population.

Mathematically, mutation is implemented as follows:

$$K_{ij}=1-K_{ij} \text{ if } q<p_M,$$

where the random number q is generated before each test.

Experimentation has concluded that the best accelerated n-tournament scheme is one that starts with n=2, with n→n+1 for each $G_{max}/10$ generations but with n not to exceed P/4.

An example of an n-tournament operation is shown at the bottom of FIG. 7. This is an example of a tournament selection from a sub-population of 4 members 710–716. With higher probability, the member 716 that has the highest ranking in dosimetric quality is replicated into the next generation member 718.

FIGS. 8A–8F display the various navigational angles affording the surgical navigation interface of the PIPER system of the present invention. The surgical scene showing the prostate, the urethra, the seed locations, the stabilizing needles, and the template is programmed in VRML (Virtual Reality Modeling Language), but is automatically generated upon completion of the planning engine.

Figure 8F:
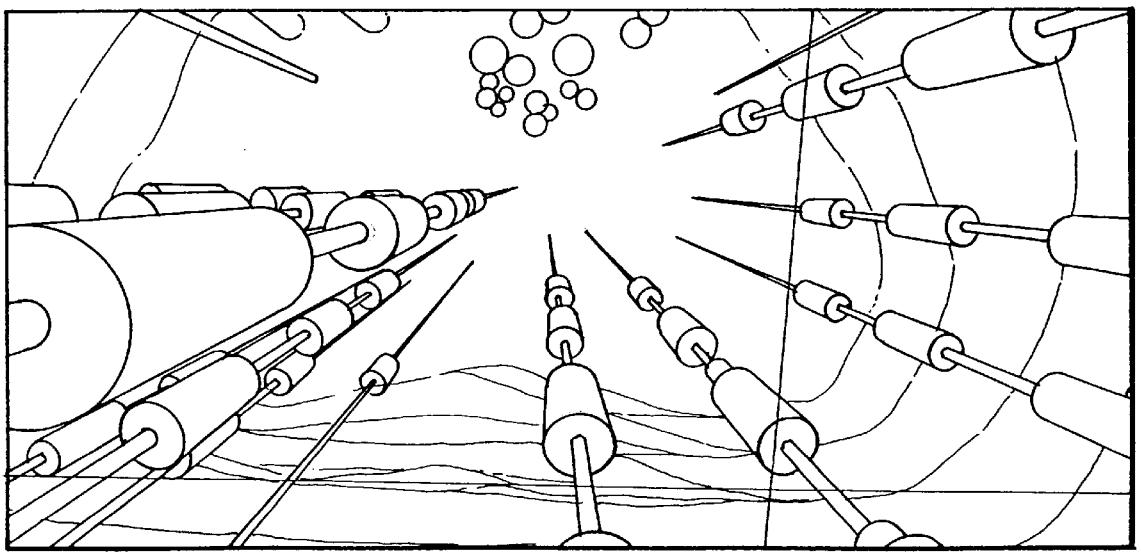
FIGS. 8A–8F are drawings of VRML model navigation used with the system of the present invention.
Figure 8A:
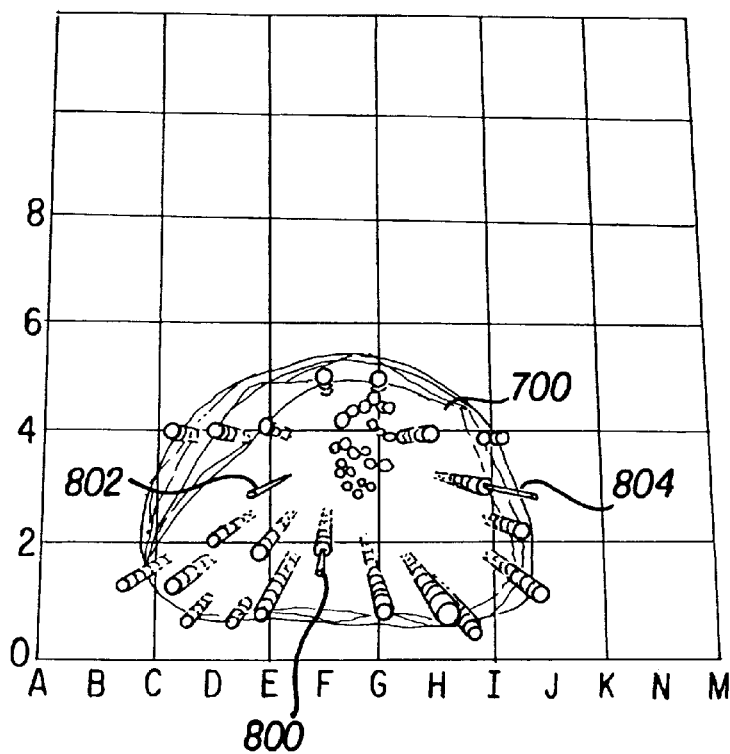
Figure 8B:
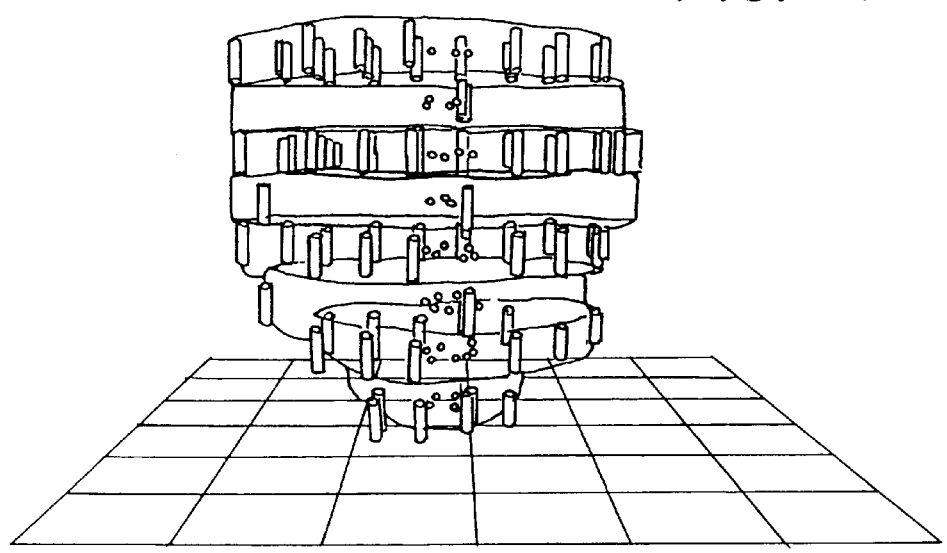
Figure 8C:
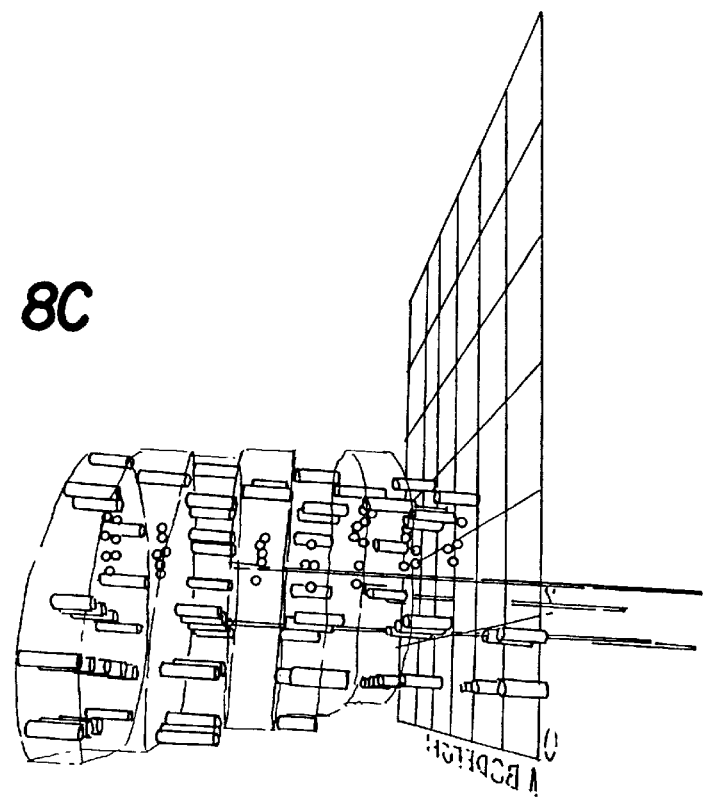
Figure 8D:
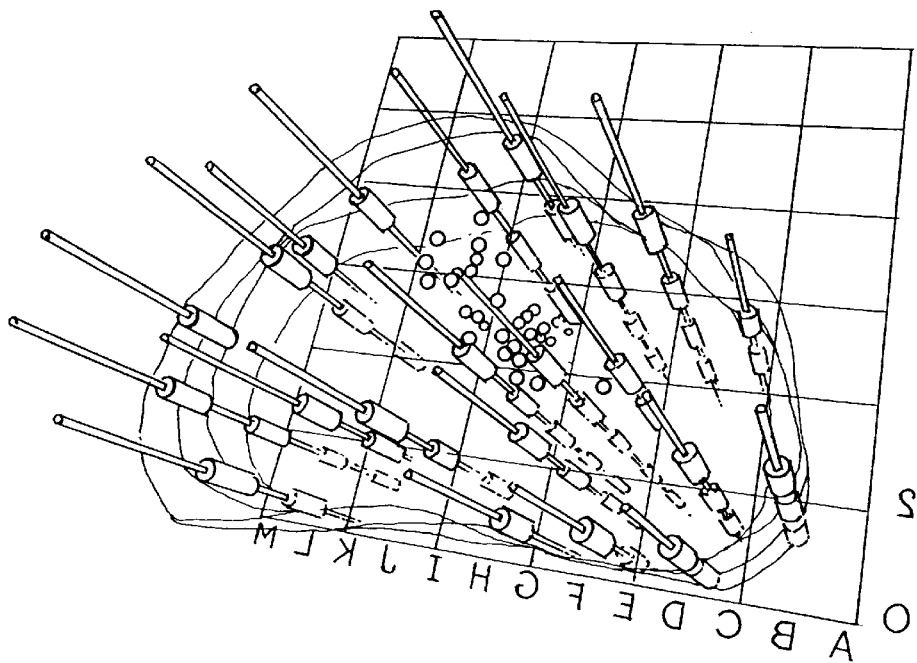

FIG. 8A shows a normal surgical view, displaying 3 stabilizing needles 800–804 at F2, E3 and I3, respectively. The horizon (showing the blue skyline) helps the clinician-user(s) to orient the scene. FIG. 8B shows an anterior view of the surgical view of FIG. 8A as displayed by an intraoperative fluoroscopic x-ray machine. FIG. 8C shows a right-to-left side view, showing the actual length of the seeds, and the prostate model as a stack of ultrasound-based slices. FIG. 8D is an optional view and displays all of the needles used in connection with the treatment plan.

Figure 8E:
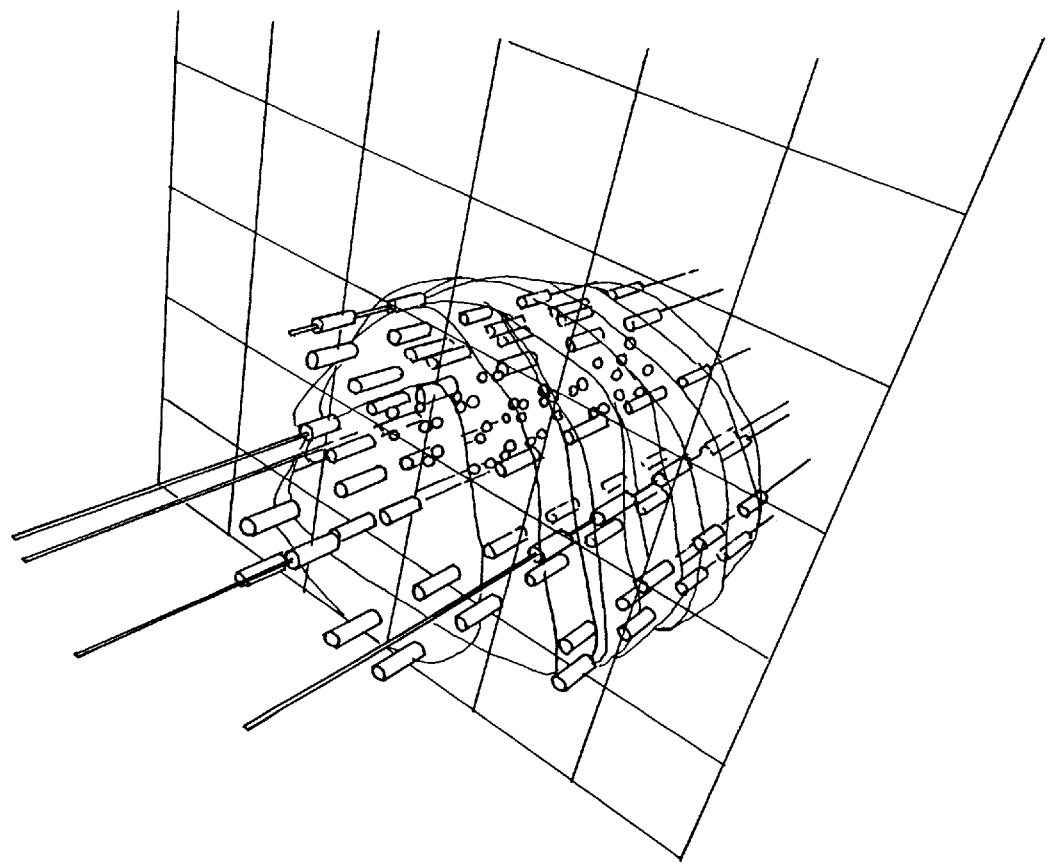

FIG. 8E is a perspective (room) view of the treatment plan for the subject prostate 100, showing the placement of all of the needles. Finally, FIG. 8F is an inside view of the prostate 100, urethra and seed trains.

The uniqueness of this navigational subsystem, in contrast to prior 3D computer displays, is that the viewer assumes an active standing position that also belongs to the scene. Various viewports are programmed relative to the usual surgical positions, such as "Surgeon View", "Room View", "AP View" etc. In addition, the user can "switch on" any seed train to pulsating colors as the pertinent needle is being placed. The relative position of the pulsating seed train from the prostate surface is used for comparison with real-time ultrasound images to verify the actual placement of the needle.

The usefulness of the virtual reality navigational model is twofold: first, clinicians find the visual confirmation of needle placement within the prostate to be extremely helpful for "feeling" the correct needle puncture technique (pressure, depth, tilt etc.); and, second, at the end of the implantation procedure, the anterior-posterior view of the navigational model can be compared with images from a mobile overhead x-ray fluoroscopy machine. Such a comparison facilitates the discovery of any regions of under-dosage due to unintentional seed migration, or provides confirmation that the implant has proceeded as planned. Neither of these two aspects of PIPER's usefulness has been reported by any prior systems for prostate brachytherapy.

Although VRML as a modeling language is generically available, and navigational interfaces such as Silicon Graphics Inc's Cosmo Player or Sony's Community Place are widely used, the application of those tools to construct an automatic surgical scene upon completion of treatment planning is non-obvious and of great benefit. Most notably, the notion of making a seed train pulsate in order to capture a few seconds attention of the surgeon, and subsequently subduing the color representation of those seeds already implanted so that the patient will not receive inadvertent double-dosing (that is, two seed trains implanted at the same location), has been found to be valuable after repeated clinical uses.

Figure 9B:
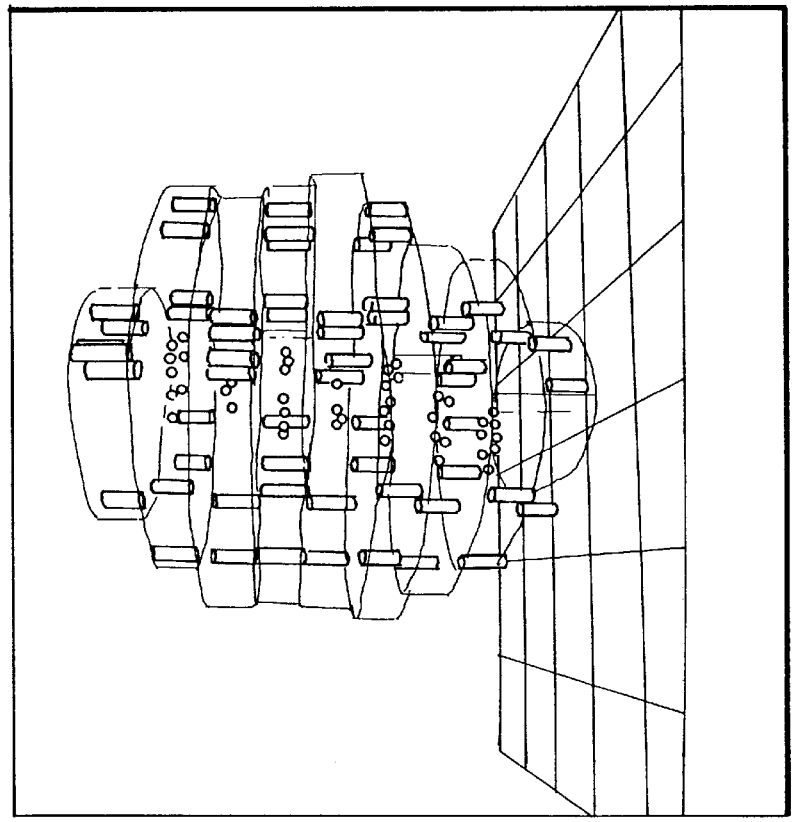
FIGS. 9A and 9B are drawings showing a comparison between a VRML model and fluoroscopic image of the prostate bearing the implanted seeds.
Figure 9A:
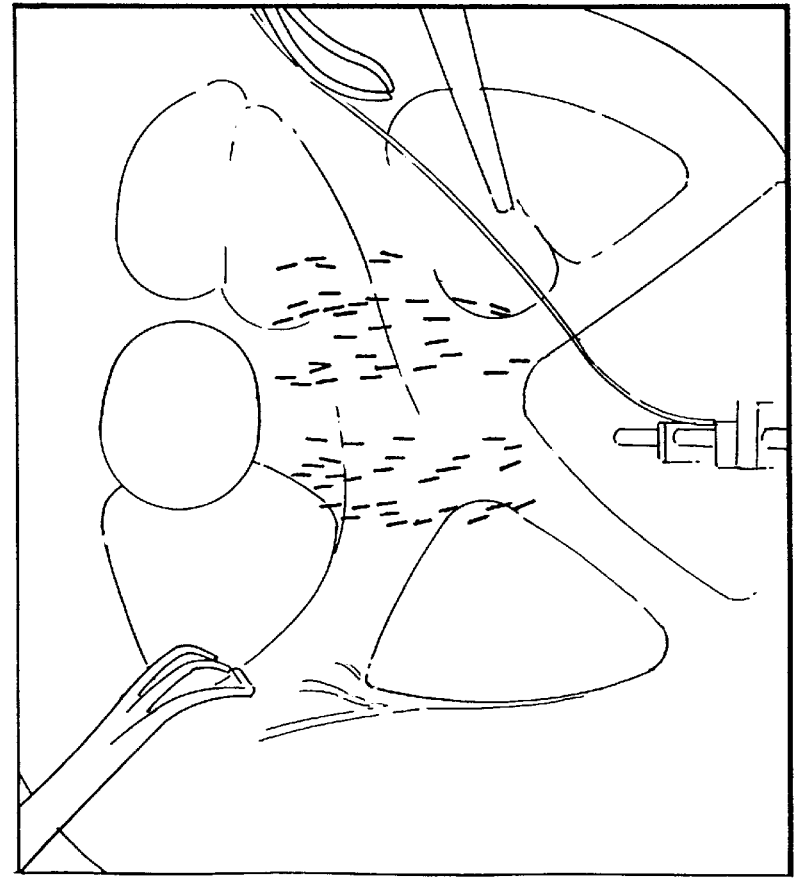

FIGS. 9A and 9B illustrate a novel use of the PIPER system's navigational model in the operating room. After implantation at all the planned seed locations, an overhead fluoroscopic x-ray image, shown in FIG. 9A, is taken of the patient's pelvic region. This image is compared with the navigational model of the same viewport, which is shown in FIG. 9B, for the approximate locations of the seeds. If certain seed trains are obscured by the straight anterior-posterior view, then both the fluoroscopic x-ray machine and the computer model can be rotated to obtain a second, stereotactic view. When such a comparison reveals that an area of gross misplacement of seeds exists that may lead to tumor under-dosage, the navigational model of FIGS. 8A–F and 9B is interrogated to determine the best needle location for remedial implantation. Importantly, such needle implantation must not disturb any existing seed placement and yet should provide an adequate dosimetric remedy. Any additional seed placement can only take place before the patient recovers from anesthesia or indeed changes position on the operating table, for the incremental cost of re-preparing the patient for additional seed placement is prohibitively high. Furthermore, permanent seed implantation cannot be altered for the life of the patient, and adding more seeds at some time after the initial implantation (for example, when an under-dosage is discovered later) is not feasible because the radioactivity of the initially placed seeds would have decayed substantially.

Figure 10:
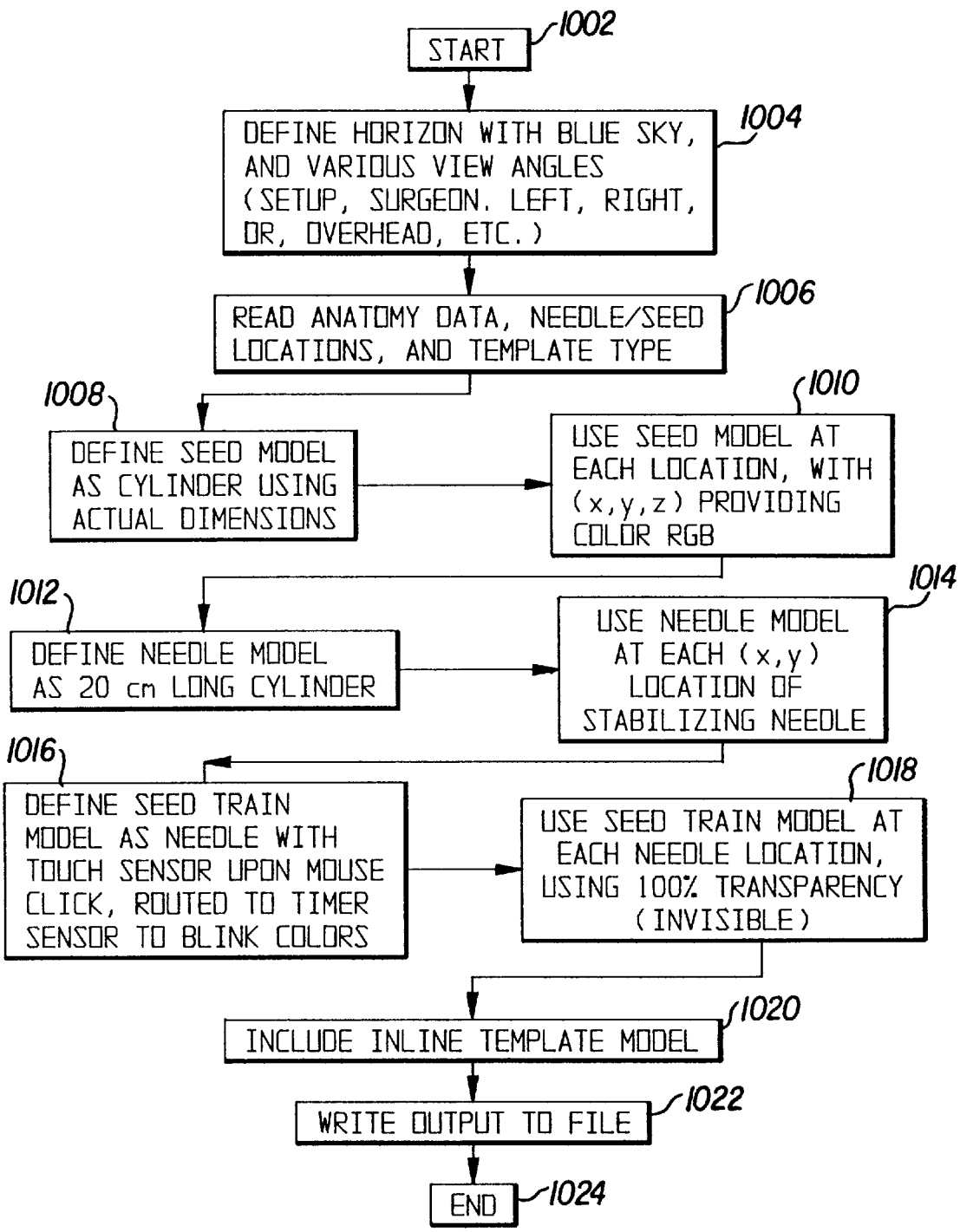
FIG. 10 is a diagram of a flow chart of the computer code that generates the VRML model from the set of basic data which result from the genetic algorithm-based planning of the present invention.

FIG. 10 is a flow chart which illustrates the process by which the VRML model is automatically generated upon completion of genetic algorithm-based planning. The computer code starts at step 1002, defines the horizon with blue sky (to aid clinicians' orientation) and various angles of viewing the surgical model at step 1004. The basic planning data such as anatomy contours, needle and seed coordinates and template type are read in at step 1006. The seed model is defined in step 1008, using the actual dimensions specified by the seed manufacturers. That seed model is used in step 1010 at each set of the seed coordinates, which are differentiated by color coding using x, y, z to provide the R, G, B intensities. In step 1012, the needle model is defined, similar to the seed model, by using a 20 cm length. The needle model is then applied in step 1014 to visualize the stabilizing needles at each of the stabilizing needle coordinates (x, y).

In step 1016, the seed train model is defined, similar to the needle model, but utilizing the touch sensor and timer sensor functions of the VRML language to enable a train of seeds to pulsate in color upon a mouse click over it. That model is then used in step 1018 at each of the needle coordinates (x, y), using a 100% transparency to make the seed train needle invisible. The purpose of doing so is to make the train of seeds pulsate without showing the connecting needle itself, while allowing the user to click anywhere along the needle projection to enable the pulsation. The VRML template model, shown at step 1020, was generated by the designer of the present system based on actual dimensions and measurements in accordance with the specifications of the actual template. The output from all the above steps is then written to the output file in step 1022, which can be read directly by the VRML browser. Finally, the computer program ends at step 1024.

In summary, the surgical scene includes the prostate, the implantation template with labeling, the planned needle positions, and the actual relative size and locations of the seeds in emissive colors. As each seed train is implanted into the patient via a needle, the emissivity of the seeds can be switched off, thus avoiding unintentional duplicate implantation at the same location. The critical anatomical structures such as the prostatic urethra are shown in prominent colors, so that clinicians can avoid them surgically. To aid orientation, the surgical scene is shown on a natural horizon that mimics the operating room view. A set of viewports are defined, including room view, surgeon view and anterior-posterior view (for comparison with x-ray fluoroscopy verification).

The surgical scene is continuously navigated and compared with the planar view of the real-time ultrasound image. That serves to verify the actual needle location relative to the prostate with respect to the treatment plan.

The capability of performing real-time verification of the surgical results before the end of the clinical procedure is a great advantage. No prior art system of treatment planning or surgical navigation is known which affords that capability.

Although only a preferred embodiment is specifically illustrated and described herein, it will be appreciated that many modifications and variations of the present invention are possible in light of the above teachings and within the preview of the appended claims without departing from the spirit and intended scope of the invention.

What is claimed is:

1. A method for intraoperative treatment planning for prostate seed implant therapy, comprising the steps of:

setting up a patient who is to receive prostate seed implant therapy in an operating room;

determining at least one of the position and volume of the patient's prostate; and determining the optimal placement of said prostate seeds to be implanted;

wherein each of said steps recited above is performed in sequence one after the other in real time while the patient is in the operating room;

and further including the step of determining the degree of pubic arch interference inherent in the determination of the placement of said prostate seeds to be implanted.

2. The method of claim 1, further including the step of modifying said determination of the placement of said prostate seeds to be implanted based upon a predetermined degree of pubic arch interference.

3. A method for the real time intraoperative treatment planning for prostate seed implant therapy in which said seeds are carried by needles comprising the steps of:

determining at least one of the position and volume of a patient's prostate;

generating a surgical template representative of said prostate;

encoding a two-dimensional binary pattern representative of all potential needle placement positions within said surgical template; and calculating the optimal solution of needle and seed locations for treatment of said prostate;

generating a three-dimensional virtual surgical scene for displaying visual confirmation of needle placement within said prostate;

inserting said needles in said prostate; and comparing actual needle placement using an x-ray device to said visual confirmation of said needle placement shown by said virtual surgical scene.

4. A method for the real time intraoperative treatment planning for prostate seed implant therapy in which said seeds are carried by needles, comprising the steps of:

determining at least one of the position and volume of a patient's prostate;

generating a surgical template representative of said prostate;

encoding a two-dimensional binary pattern representative of all potential needle placement positions within said surgical template;

calculating the optimal solution of needle and seed locations for treatment of said prostate; and determining the degree of pubic arch interference present in said optimal solution of needle and seed locations.

5. A method for the real time intraoperative treatment planning for prostate seed implant therapy in which said seeds are carried be needles, comprising the steps of:

determining at least one of the position and volume of a patient's prostate;

generating a surgical template representative of said prostate;

encoding a two-dimensional binary pattern representative of all potential needle placement positions within said surgical template;

calculating the optimal solution of needle and seed locations for treatment of said prostate; and generating a three-dimensional virtual surgical scene for displaying visual confirmation of needle placement within said prostate;

wherein said surgical scene is shown in a natural horizon that mirrors an operating room view.

6. The method of claim 4, further including the step of modifying said optimal solution of needle and seed locations based upon a predetermined degree of pubic arch interference.

7. A system for the real time intraoperative treatment planning for prostate seed implantation therapy, comprising:

an operating room for setting up a patient whose prostate is to be treated with said prostate seed implantation therapy;

means for determining at least one of the position and volume of said prostate and for generating a surgical implantation template representative of said prostate;

means for determining the optimal placement of prostate seeds to be implanted;

a three-dimensional virtual surgical scene for displaying said prostate, said surgical implantation template and optimal placement of said prostate seeds to be implanted; and means for determining the degree of pubic arch interference present in said optimal solution of said prostate seeds to be implanted.

8. A system for the real time intraoperative treatment planning for prostate seed implantation therapy, comprising:

an operating room for setting up a patient whose prostate is to be treated with said prostate seed implantation therapy;

means for determining at least one of the position and volume of said prostate and for generating a surgical implantation template representative of said prostate;

means for determining the optimal placement of prostate seeds to be implanted;

a three-dimensional virtual surgical scene for displaying said prostate, said surgical implantation template and optimal placement of said prostate seeds to be implanted; and means for modifying said optimal solution of said prostate seeds to be implanted based upon a predetermined degree of pubic arch interference;

wherein said virtual surgical scene is continuously navigated and compared with a real-time ultrasound image of the surgical scene for verification of said prostate seed implantation in said prostate relative to the determined optimal placement of said prostate seeds.

9. A method for the real time intraoperative treatment planning for seed implant therapy in which said seeds are carried by needles, comprising the steps of:

determining at least one of the position and volume of a patient's organ to be treated;

generating a surgical template representative of said organ;

encoding a two-dimensional binary pattern representative of all potential needle placement positions within said surgical template;

calculating the optimal solution of needle and seed locations for treatment of said organ;

generating a three-dimensional virtual surgical scene for displaying visual confirmation of needle placement within said organ;

inserting said needles in said organ; and comparing actual needle placement using an x-ray device to said visual confirmation of said needle placement shown by said virtual surgical scene.

* * * * *